US006858769B2

(12) United States Patent
Woodle et al.

(10) Patent No.: US 6,858,769 B2
(45) Date of Patent: Feb. 22, 2005

(54) LITHIUM ALUMINATE LAYERED CATALYST AND A SELECTIVE OXIDATION PROCESS USING THE CATALYST

(75) Inventors: Guy B. Woodle, Mount Prospect, IL (US); Andrew S. Zarchy, Kildeer, IL (US); Jeffery C. Bricker, Buffalo Grove, IL (US); Andrzej Z. Ringwelski, Marengo, IL (US)

(73) Assignee: UOP LLC, Des Plaines, IL (US)

( * ) Notice: Subject to any disclaimer, the term of this patent is extended or adjusted under 35 U.S.C. 154(b) by 113 days.

(21) Appl. No.: 10/274,693

(22) Filed: Oct. 18, 2002

(65) Prior Publication Data

US 2004/0077911 A1 Apr. 22, 2004

(51) Int. Cl.$^7$ .................... C07C 5/42; C07C 5/333; B01J 23/58; C10G 47/10; C10G 47/14
(52) U.S. Cl. .............. 585/658; 502/178; 502/304; 502/325; 502/328; 502/329; 502/330; 502/333; 502/334; 502/339; 502/332; 502/344; 502/355; 502/527.14; 502/527.15; 585/654; 585/660; 585/440; 585/443; 585/467; 585/709; 585/721; 585/664; 585/670; 585/671; 585/734; 585/750; 585/477; 585/480; 585/482; 585/250; 585/266; 585/267; 585/268; 585/269; 585/648; 585/653; 585/752; 208/106; 208/107; 208/108; 208/112; 208/113; 208/121; 208/122; 208/124
(58) Field of Search ................ 502/178, 304, 502/325, 328, 329, 330, 333, 334, 339, 332, 344, 355, 527.14, 527.15; 585/654, 658, 660, 440, 443, 467, 709, 721, 664, 670, 671, 734, 750, 477, 480, 482, 250, 266, 267, 268, 269, 648, 653, 752; 208/106, 107, 108, 112, 113, 121, 122, 124

(56) References Cited

U.S. PATENT DOCUMENTS

| | | | |
|---|---|---|---|
| 4,467,050 A | * 8/1984 | Patel et al. | 502/330 |
| 4,565,898 A | 1/1986 | O'Hara et al. | 585/441 |
| 4,812,597 A | 3/1989 | Imal et al. | 585/443 |
| 4,914,249 A | 4/1990 | Benedict | 585/443 |
| 5,146,013 A | 9/1992 | Dogimont et al. | 570/101 |
| 5,536,695 A | 7/1996 | Biéejean et al. | 502/327 |
| 5,885,917 A | 3/1999 | Ohdan et al. | 501/153 |
| 6,177,381 B1 | 1/2001 | Jensen et al. | 502/325 |
| 6,388,154 B1 | 5/2002 | Hamana et al. | 585/441 |

* cited by examiner

Primary Examiner—Elizabeth D. Wood
(74) Attorney, Agent, or Firm—John G. Tolomei; Frank S. Molinaro

(57) ABSTRACT

A catalyst for the selective oxidation of hydrogen has been developed. It comprises an inert core such as cordierite and an outer layer comprising a lithium aluminate support. The support has dispersed thereon a platinum group metal and a promoter metal, e.g. platinum and tin respectively. This catalyst is particularly effective in the selective oxidation of hydrogen in a dehydrogenation process.

25 Claims, 2 Drawing Sheets

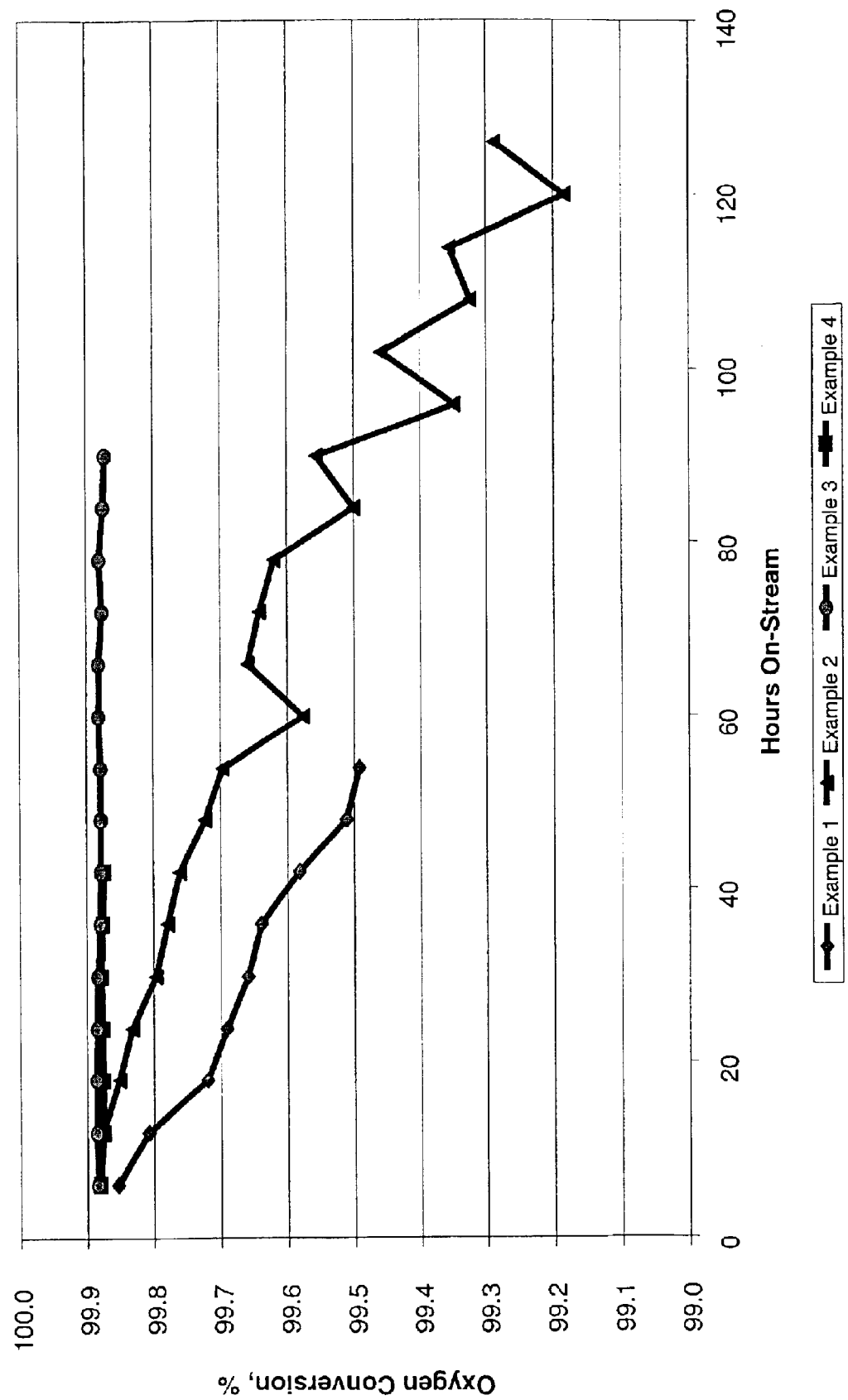

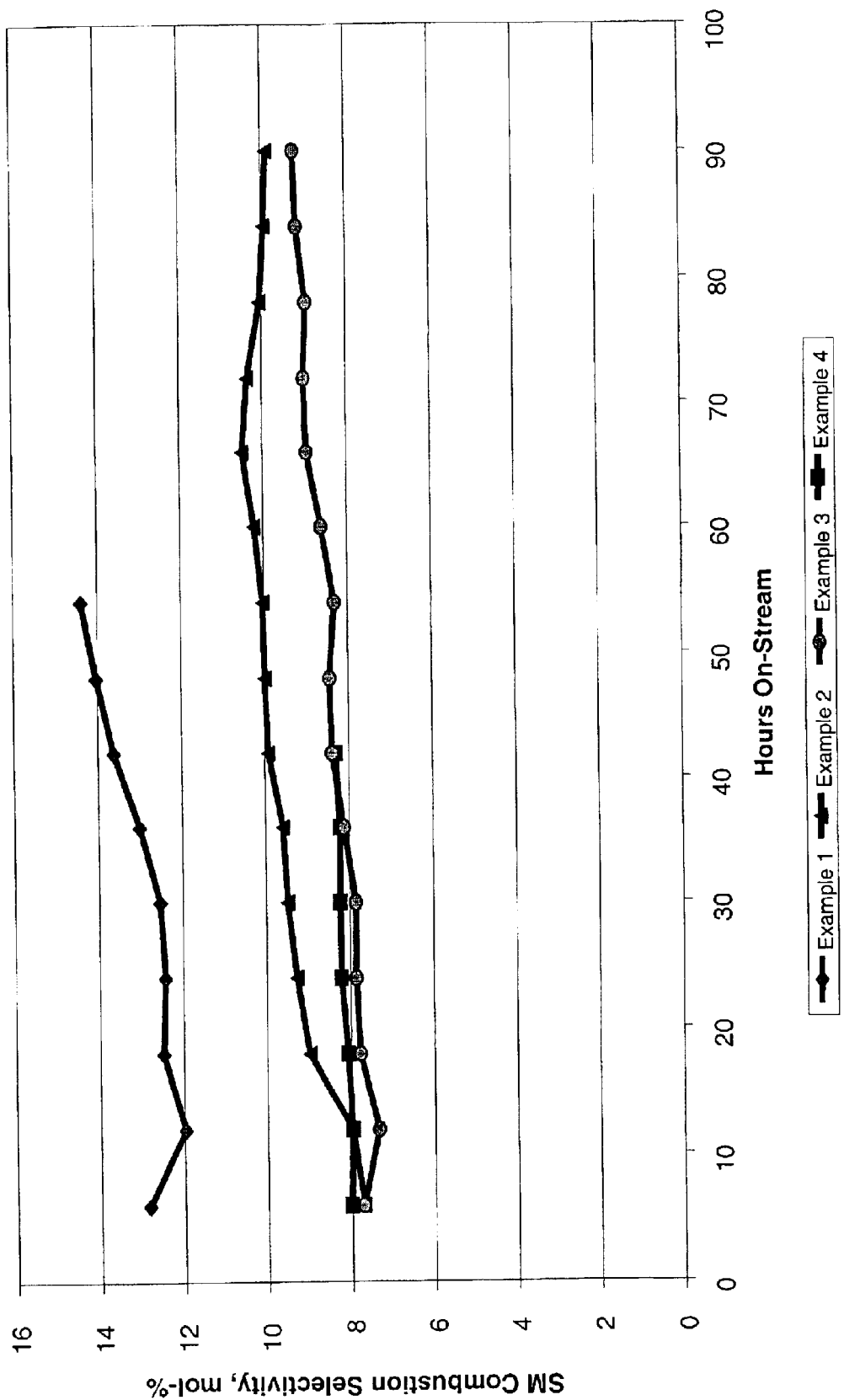

LITHIUM ALUMINATE LAYERED CATALYST AND A SELECTIVE OXIDATION PROCESS USING THE CATALYST

FIELD OF THE INVENTION

This invention relates to a selective oxidation catalyst comprising an inert core, e.g. cordierite, and an outer layer comprising a lithium aluminate support. On the support are dispersed a platinum group metal and a promoter metal, e.g. tin. The catalyst is used to selectively oxidize hydrogen in a dehydrogenation process.

BACKGROUND OF THE INVENTION

The dehydrogenation of dehydrogenatable hydrocarbons to produce unsaturated hydrocarbons is well known in the art. The typical process involves contacting the dehydrogenatable hydrocarbon with a dehydrogenation catalyst under dehydrogenation conditions to produce a mixture of dehydrogenated compounds and unconverted hydrocarbons. Usually the dehydrogenation is carried out in the presence of steam with the liberation of hydrogen. It is also known that dehydrogenation, for example ethylbenzene to styrene, is endothermic in nature and thus the temperature of the catalyst bed decreases significantly during the progress of the reaction, thus lowering the conversion of ethylbenzene to styrene. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level but also the selectivity for styrene since at equilibrium conditions only undesirable side reactions continue to take place. One method found in the art for maintaining the reaction temperature is to introduce oxygen or an oxygen containing gas which will burn the hydrogen formed during the dehydrogenation reaction thus increasing the temperature of the effluent stream and consequently increasing the conversion of the ethylbenzene to styrene.

The combustion or oxidation of hydrogen with oxygen takes place in the presence of an oxidation catalyst. A number of oxidation catalysts are known in the art. For example in U.S. Pat. No. 4,914,249 an oxidation catalyst is described which comprises a solid porous support such as alumina which has been impregnated with a Group VIII noble metal such as platinum, a Group IVA metal such as tin followed by calcining of the impregnated support and finally impregnating the calcined support with a compound containing lithium followed by a final calcination. The patentees claim that such a catalyst has superior stability and performance than previous catalysts. In U.S. Pat. No. 4,565,898 an oxidation catalyst is described which comprises a Group VIII noble metal, a Group IVA metal and a Group I or II metal dispersed on an alumina support which has been calcined at a temperature in the range from about 900° C. to about 1500° C.

In contrast to this art applicants have developed a catalyst for the selective oxidation of hydrogen in a dehydrogenation process which uses a lithium aluminate as the support for the catalytic metals. Additionally, applicants' catalyst is a layered catalyst comprising an inert inner core such as cordierite and an outer layer of a lithium aluminate bonded to the inner core and having the catalytic metals, e.g., platinum and tin dispersed only on the outer layer.

Layered catalysts are also known in the art as for example in U.S. Pat. No. 6,177,381 which discloses a layered catalyst having an inert inner core and an outer layer where the outer layer can be a refractory inorganic oxide and can optionally contain an alkaline metal. However, there is no mention in the '381 patent of having a layer composed of lithium aluminate.

SUMMARY OF THE INVENTION

As stated the present invention relates to a selective oxidation catalyst and to a process for using the catalyst. Accordingly, one embodiment of the invention is a catalyst for the selective oxidation of hydrogen comprising an inert inner core and an outer layer bonded to the inner core, the outer layer comprising a lithium aluminate support having dispersed thereon at least one platinum group metal and at least one promoter metal.

Another embodiment of the invention is a process for the dehydrogenation of a dehydrogenatable hydrocarbon comprising: (a) contacting the hydrocarbon with a dehydrogenation catalyst in the presence of steam in a dehydrogenation zone at dehydrogenation conditions to produce an effluent stream comprising dehydrogenated hydrocarbons, unconverted hydrocarbons, hydrogen and steam; (b) flowing the effluent stream to an oxidation zone and contacting the effluent stream with an oxygen containing gas in the presence of an oxidation catalyst at oxidation conditions to selectively oxidize the hydrogen in the effluent stream without substantial oxidation of the dehydrogenated and unconverted hydrocarbons and produce a second effluent stream comprising dehydrogenated hydrocarbons, unconverted hydrocarbons and steam, the oxidation catalyst comprising an inert inner core and an outer layer bonded to the inner core, the outer layer comprising a lithium aluminate support having dispersed thereon at least one platinum group metal and at least one promoter metal; (c) flowing the second effluent stream to a second dehydrogenation zone operated at dehydrogenation conditions and containing a dehydrogenation catalyst to produce a dehydrogenated hydrocarbon product stream.

These and other objects and embodiments will become more clear after a detail description of the invention.

BRIEF DESCRIPTION OF THE DRAWINGS

FIG. 1 presents plots of oxygen conversion versus hours on stream for catalysts containing varying amounts of lithium.

FIG. 2 presents plots of styrene monomer (SM) combustion selectivity versus hours on stream for catalysts containing varying amounts of lithium.

DETAILED DESCRIPTION OF THE INVENTION

One aspect of the present invention is a layered catalyst for the selective oxidation, i.e. combustion, of hydrogen in a hydrocarbon dehydrogenation process. The layered catalyst comprises an inner core composed of a material which has substantially little adsorptive capacity for catalytic metal precursors. The inner core material may be selected from the group consisting of alpha alumina, metals, silicon carbide, cordierite and mixtures thereof. Cordierite is a preferred inner core material.

These materials which form the inner core can be formed into a variety of shapes such as pellets, extrudates, spheres or irregularly shaped particles although not all materials can be formed into each shape. Preparation of the inner core can be done by means known in the art such as oil dropping, pressure molding, metal forming, pelletizing, granulation, extrusion, rolling methods and marumerizing. A spherical inner core is preferred. The inner core whether spherical or not has an effective diameter of about 0.05 mm to about 10 mm and preferably from about 0.8 mm to about 5 mm. For a non-spherical inner core, effective diameter is defined as the diameter the shaped article would have if it were molded into a sphere.

Next, an alumina layer is applied to the inner core by forming a slurry of the alumina using means well known in the art, which usually involves the use of a peptizing agent. Specifically, the alumina can be mixed with water and an acid such as nitric, hydrochloric or sulfuric to give a slurry. Alternatively, an aluminum sol can be made by for example dissolving aluminum metal and hydrochloric acid and by mixing the aluminum sol with an alumina powder. The alumina can be either gamma alumina or theta alumina.

The slurry may optionally contain an organic bonding agent which aids in the adhesion of the layer material to the inner core. Examples of this organic bonding agent include but are not limited to polyvinyl alcohol (PVA), hydroxy propyl cellulose, methylcellulose and carboxy methylcellulose. The amount of organic bonding agent which is added to the slurry will vary considerably from about 0.1 wt. % to about 3 wt. % of the slurry.

Depending on the particle size of the alumina, it may be necessary to mill the slurry in order to reduce the particle size and simultaneously give a narrower particle size distribution. This can be done by means known in the art such as ball milling for times of about 30 minutes to about 5 hours and preferably from about 1.5 to about 3 hours.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 40 to about 400 microns, preferably from about 40 to about 300 microns and most preferably from about 50 microns to about 200 microns. Once the inner core is coated with the layer of alumina, the resultant layered support is dried at a temperature of about 100° C. to about 350° C. for a time of about 1 to about 24 hours and then calcined at a temperature of about 400° C. to about 1300° C., preferably from about 600° C. to about 1200° C. and more preferably from about 750° C. to about 1050° C. for a time of about 0.5 to about 10 hours to effectively bond the outer layer to the inner core. Of course, the drying and calcining steps can be combined into one step.

In order to form the lithium aluminate support, the alumina layered composition is now impregnated with a lithium compound such as lithium chloride, lithium nitrate, lithium acetate, lithium bicarbonate, etc. The layered composition is impregnated with a solution containing a lithium compound in an amount sufficient to provide a lithium concentration on the outer layer which upon calcination will convert the alumina to substantially all lithium aluminate. By substantially all is meant at least 50 wt. % and preferably at least 75 wt. % lithium aluminate. This amount can vary from about 1:5 molar ratio of Li:Al to about 1:1 molar ratio of Li:Al. Although the ratio of Li:Al can be increased above 1:1, more moles of Li than Al, it is generally not preferred. In terms of weight % of lithium (on an elemental basis) on the outer layer of the finished catalyst the range is from about 1 wt. % to about 11 wt. %. Thus, when lithium aluminate is used herein it is meant to have the same meaning as substantially all lithium aluminate as defined above.

A preferred impregnation procedure involves the use of a steam jacketed rotary dryer. The support is immersed in the impregnating solution contained in the dryer and containing the desired lithium compound and the support is tumbled therein by the rotating motion of the dryer. Evaporation of the solution in contact with the tumbling support is expedited by applying steam to the dryer jacket. The resultant composite is allowed to dry under ambient temperature conditions or dried at a temperature of about 80° C. to 110° C. followed by calcination at a temperature of about 400° C. to about 1300° C. preferably from about 600° C. to about 1200° C. and most preferably from about 750° C. to about 1050° C. for a time of about 1 hour to about 24 hours thereby forming lithium aluminate.

An alternate process of coating the inner core with lithium aluminate is to first impregnate an alumina (gamma or theta) with a solution containing a lithium compound at the desired concentration. Again this can be done by means well known in the art as set forth above. The lithium containing alumina is now dried at a temperature of about 100° C. to about 350° C. At this point the dried lithium containing alumina can either be calcined as stated above to form lithium aluminate or slurried and applied to the inner core as described above. If a slurry is prepared prior to calcination, then once the layer is formed on the core material, the layered composite is dried and calcined to form the lithium aluminate. When lithium aluminate is formed prior to its application onto the inner core, the lithium aluminate is slurried and coated onto the inner core by the same procedure described above for alumina. Again the lithium aluminate layered support is dried and calcined at a temperature of about 400° C. to about 1300° C. for a time of about 1 hour to about 24 hours in order to bond the lithium aluminate layer to the core.

Next, a platinum group metal is dispersed on the lithium aluminate layered support by impregnation means as described above. Thus, the lithium aluminate layered composition can be impregnated with a solution (preferably aqueous) containing a decomposable compound of the metal or metals. By decomposable is meant that upon heating the metal compound is converted to the metal or metal oxide with the release of byproducts. The lithium aluminate containing a platinum group metal can be dried at a temperature of about 80° C. to about 110° C. followed by calcination at a temperature of about 200° C. to about 700° C. for a time of about 1 to about 4 hours, thereby converting the metal compound to the metal or metal oxide. The platinum group metal is present in an amount from about 0.005 to about 5 wt. % of the catalyst, i.e. inner core plus outer layer.

The promoter metal can now be impregnated in a similar way to that described for the platinum group metal. Promoter metals are selected from the group consisting of tin, germanium, rhenium, gallium, bismuth, lead, indium, serium, zinc and mixtures thereof. Illustrative of the decomposable promoter metal compounds are the halide salts of the promoter metals. A preferred promoter is tin and preferred decomposable compounds are stannous chloride or stannic chloride. The promoter metal and platinum group metal can be simultaneously impregnated from a common solution. Further, the platinum group metal and promoter metal can be dispersed either on the alumina (before or after the alumina is deposited on the inner core), the alumina impregnated with a lithium compound or lithium aluminate prior to the formation of a slurry and coating of the inner core or on the layered composite where the outer layer is lithium aluminate. Although the catalytic metals may be dispersed onto the lithium aluminate in a number of ways, equivalent catalysts are not necessarily obtained from each procedure. A convenient way to prepare the catalyst is to first coat the inert core with alumina containing a promoter metal component. After drying and calcining, the coated core is impregnated using a solution comprising a platinum group metal compound and a lithium compound as described above. The impregnated composite is then heated as described above to form lithium aluminate. The amount of promoter metal is present in an amount from about 0.005 to about 5.0 wt. % of the catalyst.

An optional modifier metal may also be dispersed on the lithium aluminate. This modifier is selected from the group consisting alkali metals, alkaline earth metals and mixtures thereof. Preferred modifier metals are sodium, lithium, cesium, barium and mixtures thereof. These modifier metals can be deposited on the lithium aluminate either before or after dispersion of the platinum group metals, although not with equivalent results. The modifier metals are deposited onto the lithium aluminate by the same methods as described for the platinum group metals or promoter metals. Effective amounts of promoter metals can vary widely but is usually between about 0.1 and 5 wt. % of the catalyst.

As stated the catalyst described above is used to selectively oxidize (combust) hydrogen as part of a dehydrogenation process. In a typical process, a dehydrogenatable hydrocarbon is contacted with a dehydrogenation catalyst in the presence of steam in a multicatalyst bed system. The dehydrogenation catalyst and selective oxidation catalyst can be disposed as alternate layers or beds in one reactor or can be in separate reactors. The number of alternate layers of dehydrogenation catalyst and oxidation catalyst can vary depending on the size and type of apparatus which is employed, the total number of layers ranging from three to about nine.

The dehydrogenation catalysts which can be used in the present process are any of those well known in the art including those described in U.S. Pat. Nos. 3,387,053; 4,467,046; 4,914,249 and 4,599,471 which are incorporated by reference in their entirety. For completeness, these dehydrogenation catalysts are described below. A common dehydrogenation catalyst is one comprising an iron compound and an alkali or alkaline earth metal. The alkali and alkaline earth metal are selected from the group consisting of lithium, sodium, potassium, rubidium, cesium, beryllium, magnesium, calcium, strontium, barium and mixtures thereof. In addition the dehydrogenation catalyst may optionally contain a compound containing at least one metal selected from Groups IVB, VB and VIB (IUPAC 4, 5, 6 respectively) of the Periodic Table of the Elements. Preparation of these catalysts is also well known and is described in the patents cited above. Usually the various compounds in the desired ratios are mixed, formed into a desired shape, e.g. extrudates and then dried to form the catalyst.

The hydrocarbons which can be dehydrogenated vary widely and include without limitation ethylbenzene, diethylbenzene, ethyl toluene, propylbenzene, isopropylbenzene, paraffins, especially $C_2$–$C_{16}$ paraffins, etc. A preferred hydrocarbon is ethylbenzene which on dehydrogenation provides styrene which has a large number of commercial uses, e.g. polymerization to polystyrene. In the description which follows ethylbenzene will be used to represent a dehydrogenatable hydrocarbon. This is done only by way of example and is not intended to exclude from the scope of the invention any of the alkylaromatic and paraffinic hydrocarbons generally set forth above.

Dehydrogenation conditions in general include a temperature of about 500° C. to about 750° C. and preferably from about 540° C. to about 675° C. The process is carried out at pressures ranging from about 10 kPa to about 1013 kPa and preferably from about 20 kPa to about 150 kPa. Of course the exact temperature and pressure will depend on the feed hydrocarbon and the activity of the catalyst. The hydrocarbon feed stream is fed through the catalyst beds to give a Liquid Hourly Space Velocity (LHSV) based on liquid hydrocarbon charge from about 0.1 to 10 $hr^{-1}$ and preferably from about 0.5 to about 2 $hr^{-1}$.

Another component of the dehydrogenation step is steam. Steam is mixed with the hydrocarbon stream in an amount to give a weight ratio of steam to hydrocarbon from about 0.5:1 to about 40:1 and preferably from about 1:1 to about 3:1.

After passing through the dehydrogenation zone, the effluent stream from that zone will comprise dehydrogenated hydrocarbon, unconverted hydrocarbon, steam and hydrogen. This effluent stream is now contacted in an oxidation zone with the selective oxidation catalyst described above. An oxygen containing gas is fed into the oxidation zone in order to selectively oxidize the hydrogen and reheat the effluent stream. Examples of oxygen containing gas include but are not limited to air, oxygen and oxygen diluted with other gases such as steam, carbon dioxide, nitrogen, argon, helium, etc. The amount of oxygen introduced into the oxidation zone ranges from about 0.1:1 to about 2:1 moles of oxygen per mole of hydrogen in the effluent stream. Temperature and pressure conditions are the same as set forth above for the dehydrogenation step. Under these conditions, hydrogen is oxidized or combusted to water without any substantial oxidation of the unconverted hydrocarbon or dehydrogenated hydrocarbon.

A second effluent stream from the oxidation zone comprising unconverted hydrocarbon, dehydrogenated hydrocarbon and steam is now flowed to a second dehydrogenation zone to further dehydrogenate the hydrocarbon. A product stream which comprises primarily dehydrogenated hydrocarbon is now recovered and can be further treated by well known means to obtain a purified dehydrogenated hydrocarbon, e.g. styrene stream.

In the event that substantial amounts of unconverted hydrocarbons are present in the effluent stream from the second dehydrogenation zone, the effluent can be flowed to a second selective oxidation zone and then a third dehydrogenation zone. This alternating of dehydrogenation and oxidation zones can be continued as necessary but usually the total number of zones or beds varies from 3 to about 9. As also stated above, each zone can be housed in separate reactors, although this is not preferred.

In addition to the oxidation of hydrogen, the catalysts of this invention can catalyze other oxidation reactions including:

1) partial oxidation of hydrocarbon streams, such as naphtha or methane, to generate synthesis gas (CO+ $H_2$); and
2) oxidation of methane, ethane or carbon monoxide to clean up flue gas emissions from combustion processes.

The instant catalyst can also catalyze hydrocarbon conversion processes including but not limited to alkylation of both aromatics and isoparaffins, hydrocracking, cracking, isomerization, hydrogenation and dehydrogenation.

The conditions necessary to carry out alkylation of aromatic compounds are well known and are disclosed, for example, in U.S. Pat. Nos. 3,965,043 and 3,979,331 which are incorporated by reference. Generally the process can be carried out in a batch type or a continuous type operation. In a batch type process, the catalyst, aromatic compound and alkylating agent are placed in an autoclave and the pressure increased, if necessary, in order to effect the reaction in the liquid phase. An excess amount of aromatic compound should be present, preferably in a range of about 2:1 to about 20:1 moles of aromatic compound per mole of alkylating agent. The reaction is carried out at an elevated temperature since the rate of alkylation is undesirably low at room temperature. Preferably the temperature is in the range of about 40° C. to about 200° C. The process is carried out for a time of about 0.5 to about 4 hours, after which the product is separated from the starting materials by conventional means.

If it is desired to carry out the process in a continuous manner, the catalyst is placed in a reactor which is heated to the desired operating temperature and the pressure increased above atmospheric, if necessary. The aromatic compound and alkylating agent are flowed over the catalyst bed at a predetermined liquid hourly space velocity sufficient to effect alkylation. The effluent is continuously withdrawn and conventional separation means used to isolate the desired product.

Hydrocracking conditions typically include a temperature in the range of 240° C. to 649° C. (400° F.–1200° F.), preferably between about 316° C. and about 510° C. (600–950° F.). Reaction pressures are in the range of atmospheric to about 24,132 kPag (3,500 psig), preferably between about 1,379 and 20,685 kPag (200–3,000 psig). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of about 178 to 8,888 standard cubic meters per cubic meter of charge (1,000 to 50,000 standard cubic feet (scf) per barrel of charge) preferably between about 355 to about 5,333 std. $m^3/m^3$ (2,000 and 30,000 scf per barrel of charge).

The reaction zone effluent is normally removed from the catalyst bed, subjected to partial condensation and vapor-liquid separation and then fractionated to recover the various components thereof. The hydrogen and, if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the catalyst composition using feedstocks such as gas oils, heavy naphthas, deasphalted crude oil residua, etc. with gasoline being the principal desired product. Temperature conditions of about 454° C. to about 593° C. (850° to 1110° F.) LHSV values of 0.5 to 10 $hr^{-1}$ and pressure conditions of from about 0 to about 345 kPag (50 psig) are suitable.

Isomerization reactions are carried out in a temperature range of about 371° C. to about 538° C. (700–1000° F.). Olefins are preferably isomerized at temperatures of about 260° C. to about 482° C. (500° F. to 900° F.), while paraffins, naphthenes and alkyl aromatics are isomerized at temperatures of about 371° C. to 538° C. (700° F. to 1000° F.). Hydrogen pressures are in the range of about 689 to about 3,445 kPag (100 to 500 psig). Contact times usually correspond to liquid hourly space velocities (LHSV) in the range of about 0.1 $hr^{-1}$ to 10 $hr^{-1}$. Hydrogen to hydrocarbon molar ratios in the range of 1 to 20, preferably between 4 and 12.

Hydrogenation processes can be carried out using reactors and hydrogenation zones similar to the dehydrogenation process described above. Specifically, hydrogenation conditions include pressures of about 0 kPag to about 13,789 kPag, temperatures of about 30° C. to about 280° C., $H_2$ to hydrogenatable hydrocarbon mole ratios of about 5:1 to about 0.1:1 and LHSV of about 0.1 to about 20 $hr^{-1}$.

The following examples are presented in illustration of the invention and are not intended as undue limitations on the generally broad scope of the invention as set out in the appended claims.

EXAMPLE 1

A slurry was prepared by mixing 439.3 g of aluminum sol (15 wt. % $Al_2O_3$) and 118.8 g of 10% aqueous solution of polyvinyl-alcohol and 448.1 g of deionized water. To this mixture there were added 349.4 g of gamma-alumina power, which had been previously treated such that the particle size was less than 200 microns. After about 10 minutes of stirring using a mixer, 10.51 g of a 50% aqueous solution of stannic chloride ($SnCl_4$) were added to the mixture, and the slurry was ball milled for about 4 hours at ambient temperature thereby reducing the maximum particle size to less than 40 microns. This slurry was sprayed onto cordierite cores having an average diameter of about 4.0 mm by using a granulating and coating apparatus for about 19 minutes to give an outer layer of about 100 microns.

This layered spherical support was dried at 150° C. for 2 hours and then calcined at 1000° C. for 12 hours in order to further convert the gamma alumina in the outer layer into theta alumina.

The calcined layered support was impregnated with platinum and lithium using a rotary impregnator by contacting the support with an aqueous solution (1:1 solution: support volume ratio) containing a mixture of lithium nitrate solution and chloroplatinic acid solution. The impregnated catalyst was heated in the rotary impregnator until no solution remained, dried and then reduced in hydrogen at 565° C. for 2 hours. The reduced catalyst was then dried for a period of two hours at a temperature of 150° C. and then heated up to 650° C. in flowing air. At this point, the air was bubbled through water, at ambient temperature before flowing over the catalyst. This calcination was carried out for two hours and then cooled in flowing air which was not passed through the bubbler. Elemental analysis showed that this catalyst contained 0.13 wt. % platinum, 0.16 wt. % tin, and 0.07 wt. % lithium on a volatile-free basis with respect to the entire catalyst. This catalyst was recovered and identified as catalyst A. X-ray diffraction analysis indicated that the outer layer consisted primarily of theta-alumina with only trace amounts of lithium aluminate.

EXAMPLE 2

A slurry was prepared by mixing 439.3 g of an aluminum sol (15 wt. % $Al_2O_3$) and 118.8 g of a 10% aqueous solution of polyvinyl-alcohol and 448.1 g of deionized water. To this mixture there were added 349.4 g of gamma-alumina powder, which had been previously treated such that the particle size was less than 200 microns. After about 10 minutes of stirring using a mixer, 10.51 g of a 50% aqueous solution of stannic chloride ($SnCl_4$) were added to the mixture and the slurry was ball milled for about 4 hours at ambient temperature thereby reducing the maximum particle size to less than 40 microns. This slurry was sprayed onto cordierite cores having an average diameter of about 4.0 mm by using a granulating and coating apparatus for about 19 minutes to give an outer layer of about 100 microns.

This layered spherical support was dried at 150° C. for 2 hours and then calcined at 1000° C. for 12 hours in order to further convert the gamma alumina in the outer layer into theta alumina.

The calcined layered support was impregnated with platinum and lithium as described in example 1, except that elemental analysis showed that this catalyst contained 0.12 wt. % platinum, 0.14 wt. % tin and 0.32 wt. % lithium on a volatile-free basis with respect to the entire catalyst. This catalyst was recovered and identified as catalyst B. X-ray diffraction analysis showed that the outer layer consisted of substoichiometric, disordered lithium aluminate, i.e. $LiAl_5O$.

EXAMPLE 3

The procedure of Example 2 was repeated, except that the concentration of lithium nitrate solution added to the rotary impregnator was increased to result in a greater concentration of lithium on the catalyst. Elemental analysis showed that this catalyst contained 0.14 wt. % platinum, 0.16 wt. % tin and 0.72 wt. % lithium with respect to the entire catalyst. This catalyst was recovered and identified as catalyst C. X-ray diffraction analysis showed that the outer layer consisted of mixtures of lithium aluminate, i.e. $LiAlO_8$ and $LiAlO_2$.

EXAMPLE 4

An oxidation catalyst was prepared by the method of Example II of U.S. Pat. No. 4,812,597 which is incorporated by reference. Catalysts prepared according to this method have been used commercially in the production of styrene and so it provides a suitable benchmark for gauging the performance of other oxidation catalysts prepared using alternative preparation methods. Elemental analysis showed that this catalyst contained 0.20 wt. % platinum, 0.23 wt. % tin and 0.20 wt. % lithium on a volatile-free basis with respect to the entire catalyst. This catalyst was identified as catalyst D. X-ray diffraction analysis showed that the catalyst was essentially alpha-alumina.

EXAMPLE 5

The catalysts of examples 1–4 were evaluated for oxygen conversion and selectivity for oxygen reacting with hydrogen to form water. The catalysts in an amount of 50 cc were loaded into a 2.2 cm (⅞") inner diameter stainless steel reactor. The reactor was heated to an inlet temperature of 570° C. and a feedstream comprising a mixture of ethylbenzene, styrene, steam, hydrogen, oxygen and nitrogen which simulated product stream at about a 60% ethylbenzene conversion from the second dehydrogenation catalyst bed of a three dehydrogenation catalyst bed reactor system having an oxidation catalyst bed positioned between the dehydrogenation catalyst beds was fed to the reactor. The feedstream was passed over the oxidation catalyst bed at the aforesaid inlet temperature and at a rector outlet pressure of 70.9 kPa (0.7 atmospheres). The feedstream was maintained at a liquid hourly space velocity of 10.4 $hr^{-1}$. The inlet feed ratio of the feedstream of ethylbenzene/styrene/$H_2O$/$H_2$/$O_2$/$N_2$ was 0.3/0.7/9/0.45/0.13/1. In addition, the air into the catalyst bed was controlled in order to maintain a maximum temperature of 630° C. in the reactor up to a specified limit of added air. The conversion of oxygen was plotted for each test and the results are shown in FIG. 1. The styrene combustion selectivity was plotted for each test and the results are shown in FIG. 1. The styrene combustion selectivity was plotted for each test and the results are shown in FIG. 2. The test results are further summarized in Table 1 below. In this table, column I is the percent of oxygen converted and column II is the styrene combustion selectivity in mole percent.

TABLE 1

| Hours | Catalyst A | | Catalyst B | | Catalyst C | | Catalyst D | |
|---|---|---|---|---|---|---|---|---|
| On-Stream | I | II | I | II | I | II | I | II |
| 20 | 99.75 | 12.5 | 99.81 | 9 | 99.90 | 7.8 | 99.90 | 8.1 |
| 30 | 99.68 | 12.6 | 99.77 | 9.5 | 99.90 | 7.9 | 99.90 | 8.2 |
| 40 | 99.60 | 13.4 | 99.72 | 9.8 | 99.90 | 8.4 | 99.90 | 8.4 |
| 50 | 99.53 | 14.1 | 99.68 | 9.9 | 99.90 | 8.4 | — | — |
| 90 | — | — | 99.50 | 9.9 | 99.89 | 9.2 | — | — |

It is to be noted from the above table that the catalysts which were prepared with greater amounts of lithium possessed significantly higher catalytic stability and lower styrene combustion selectivity than did the other catalysts with lower amounts of lithium.

EXAMPLE 6

In order to further evaluate the performance of a catalyst prepared according to the process of this invention several of the catalysts were subjected to a hydrothermal aging process in order to determine a simulated aged activity. The catalysts were subjected to 24 hours of aging at a temperature of 750° C. and a pressure of 101.3 kPa (1 atmosphere) in the presence of an atmosphere of air and steam.

The aging process simulated a period of about 1 year of use in a commercial unit. The catalysts were then tested in a selective oxidation process. About 14 cc of catalyst was loaded into a 2.2 cm (⅞") inner diameter stainless steel reactor. The reactor was heated to an inlet temperature such that the maximum bed temperature was maintained at 600° C. and a feedstream comprising a mixture of 7.3 mole percent nitrogen, 3.9 mole percent hydrogen, 0.8 mole percent oxygen, 8.7 mole percent of a mixture of about 36% ethylbenzene and about 64% styrene plus 79.2 mole percent steam was fed to the reactor. The feedstream was passed over the oxidation catalyst beds at the aforesaid inlet temperature at a reactor outlet pressure of 70.9 kPa (0.7 atmospheres). The feed was maintained at a liquid hourly space velocity of 37 $hr^{-1}$.

As an indication of the stability and activity of the catalyst, measurements were taken periodically to determine the oxygen conversion. The results of these tests are set forth in Table 2 below:

TABLE 2

| Oxygen Conversion of Aged Catalysts (%) | | | |
|---|---|---|---|
| Hours | Catalyst | | |
| On-Stream | B | C | D |
| 6 | 93.5 | 93.5 | 95 |
| 12 | 92 | 92.5 | 94 |
| 18 | 91 | 92 | 94 |
| 24 | 91 | 92 | 93.5 |
| 42 | 91 | 92 | — |

It is to be noted that the catalysts of the present invention exhibited identical stability and activity within the constraints of this test procedure as compared against a standard catalyst.

What is claimed is:

1. A catalyst for the selective oxidation of hydrogen comprising an inert inner core and an outer layer bonded to the inner core, the outer layer comprising a lithium aluminate support having dispersed thereon at least one platinum group metal and at least one promoter metal.

2. The catalyst of claim 1 where the inert inner core is selected from the group consisting of alpha alumina, metals, silicon carbide, cordierite and mixtures thereof.

3. The catalyst of claim 1 where the platinum group metal is selected from the group consisting of platinum, palladium, rhodium, iridium, ruthenium, osmium and mixtures thereof.

4. The catalyst of claim 3 where the platinum group metal is platinum and is present in an amount from about 0.005 to about 5 wt. % of the catalyst.

5. The catalyst of claim 1 where the promoter metal is selected from the group consisting of tin, germanium, rhenium, gallium, bismuth, lead, indium, cerium, zinc and mixtures thereof.

6. The process of claim 5 where the promoter metal is tin and is present in an amount from about 0.005 to about 5 wt. % of the catalyst.

7. The catalyst of claim 1 where the outer layer has a thickness from about 40 to about 400 microns.

8. The catalyst of claim 2 where the inner core is cordierite.

9. The catalyst of claim 1 further comprising a modifier dispersed on the lithium aluminate support and selected from the group consisting of alkali metals, alkaline earth metals and mixtures thereof.

10. The catalyst of claim 9 where the modifier is selected from the group consisting of lithium, sodium, cesium, barium and mixtures thereof.

11. A process for the dehydrogenation of a dehydrogenatable hydrocarbon comprising:
   a) contacting the hydrocarbon with a dehydrogenation catalyst in the presence of steam in a dehydrogenation zone at dehydrogenation conditions to produce an effluent stream comprising dehydrogenated hydrocarbons, unconverted hydrocarbons, hydrogen and steam;
   b) flowing the effluent stream to an oxidation zone and contacting the effluent stream with an oxygen containing gas in the presence of an oxidation catalyst at oxidation conditions to selectively oxidize the hydrogen in the effluent stream without substantial oxidation of the dehydrogenated and unconverted hydrocarbons and produce a second effluent stream comprising dehydrogenated hydrocarbons, unconverted hydrocarbons and steam, the oxidation catalyst comprising an inert inner core and an outer layer bonded to the inner core, the outer layer comprising a lithium aluminate support having dispersed thereon at least one platinum group metal and at least one promoter metal;
   c) flowing the second effluent stream to a second dehydrogenation zone operated at dehydrogenation conditions and containing a dehydrogenation catalyst to produce a dehydrogenated hydrocarbon product stream.

12. The process of claim 11 where the inert inner core is selected from the group consisting of alpha alumina, metals, silicon carbide, cordierite and mixtures thereof.

13. The process of claim 11 where the platinum group metal is selected from the group consisting of platinum, palladium, rhodium, iridium, ruthenium, osmium and mixtures thereof.

14. The process of claim 13 where the platinum group metal is platinum and is present in an amount from about 0.005 to about 5 wt. % of the catalyst.

15. The process of claim 11 where the promoter metal is selected from the group consisting of tin, germanium, rhenium, gallium, bismuth, lead, indium, cerium, zinc and mixtures thereof.

16. The process of claim 15 where the promoter metal is tin and is present in an amount from about 0.005 to about 5 wt. % of the catalyst.

17. The process of claim 11 where the lithium aluminate support has dispersed thereon at least one modifier selected from the group consisting of alkali metals and alkaline earth metals.

18. The process of claim 17 where the modifier is selected from the group consisting of lithium, sodium, cesium, barium and mixtures thereof.

19. The process of claim 11 where the oxidation conditions include a temperature from about 500° to about 750° C. and a pressure from about 20 to about 150 kPa.

20. The process of claim 11 where the oxygen containing gas is air.

21. The process of claim 11 where the oxygen containing gas is a mixture of oxygen and steam.

22. The process of claim 11 where the dehydrogenatable hydrocarbon is ethylbenzene and the dehydrogenated hydrocarbon is styrene.

23. The process of claim 11 where the dehydrogenation conditions include a temperature of about 500° to about 750° C. and a pressure of about 20 to about 150 kPa.

24. A hydrocarbon conversion process comprising contacting a hydrocarbon feed with a catalyst at conversion conditions to give a converted product, where the catalyst comprises an inert inner core, an outer layer comprising a lithium aluminate support having dispersed thereon at least one platinum group metal and at least one promoter metal.

25. The process of claim 24 where the process is selected from the group consisting of alkylation, dehydrogenation, dehydrogenation and isomerization.

* * * * *